(12) United States Patent
Cerro (10) Patent No.: US 12,115,487 B1
(45) Date of Patent: Oct. 15, 2024

(54) AIR VENTILIZATION SYSTEM FILTER

(71) Applicant: Darryl Cerro, Mooresville, NC (US)

(72) Inventor: Darryl Cerro, Mooresville, NC (US)

(*) Notice: Subject to any disclaimer, the term of this patent is extended or adjusted under 35 U.S.C. 154(b) by 0 days.

(21) Appl. No.: 18/745,882

(22) Filed: Jun. 17, 2024

Related U.S. Application Data (63) Continuation-in-part of application No. 18/471,093, filed on Sep. 20, 2023, now Pat. No. 12,011,684, and a continuation-in-part of application No. 17/174,966, filed on Feb. 12, 2021, now abandoned.

(51) Int. Cl.
| | |
|---|---|
| *B01D 46/36* | (2006.01) |
| *A61L 9/013* | (2006.01) |
| *B01D 39/06* | (2006.01) |
| *B01D 46/00* | (2022.01) |

(52) U.S. Cl.
CPC .............. *B01D 46/36* (2013.01); *B01D 39/06* (2013.01); *B01D 46/0002* (2013.01); *B01D 46/0038* (2013.01); *A61L 9/013* (2013.01); *A61L 2209/14* (2013.01); *B01D 2239/1241* (2013.01); *B01D 2265/02* (2013.01); *B01D 2279/50* (2013.01)

(58) Field of Classification Search
None
See application file for complete search history.

(56) References Cited

U.S. PATENT DOCUMENTS

| | | | | | |
|---|---|---|---|---|---|
| 1,528,640 | A | * | 3/1925 | Vodicka | F24F 8/50 |
| | | | | | 261/96 |
| 2,812,900 | A | * | 11/1957 | Matthews | F16P 1/02 |
| | | | | | 416/247 R |
| 2,978,064 | A | * | 4/1961 | Deaver | B01D 39/2072 |
| | | | | | 96/151 |
| 3,262,638 | A | * | 7/1966 | Militello | F04D 29/703 |
| | | | | | D23/382 |
| 3,675,394 | A | * | 7/1972 | Sterrett | B01D 46/30 |
| | | | | | 55/518 |
| 4,285,468 | A | * | 8/1981 | Hyman | B32B 27/304 |
| | | | | | 239/55 |
| 4,968,456 | A | * | 11/1990 | Muderlak | A61L 9/122 |
| | | | | | 261/DIG. 65 |
| 5,002,462 | A | * | 3/1991 | Janisse | F04D 29/703 |
| | | | | | 416/247 R |
| 5,087,273 | A | * | 2/1992 | Ward | B01D 46/10 |
| | | | | | 239/57 |

(Continued)

*Primary Examiner* — Brit E. Anbacht
(74) *Attorney, Agent, or Firm* — QuickPatents; Kevin Prince (57) ABSTRACT

A filter assembly adaptable to various air moving systems, including HVAC units and portable fans, comprises a lower frame with a flexible mesh that, along with the frame's perimeter, encloses a volume containing particulate filter media. This media filters air while producing an audible noise indicating system operation. The upper frame, attachable to the lower frame, includes a mesh bottom and houses scenting materials to enhance air quality with fragrances, designed to prevent these materials from escaping during use. Both frames feature mechanical fasteners for easy mutual attachment and maintenance. The upper frame's mesh side is partially removable for management of scenting materials. This filter assembly offers both functional air filtration and optional air scenting, providing a versatile and user-friendly solution for improving indoor air environments.

11 Claims, 6 Drawing Sheets

(56) References Cited

U.S. PATENT DOCUMENTS

| | | | |
|---|---|---|---|
| 5,240,487 A * | 8/1993 | Kung | A61L 9/12 55/DIG. 35 |
| 5,240,653 A * | 8/1993 | Ramkissoon | A61L 9/12 422/123 |
| 5,468,447 A * | 11/1995 | Bermas | A61L 9/12 422/4 |
| 7,093,773 B2 * | 8/2006 | Kuiper | A61L 9/04 239/289 |
| 7,837,772 B2 * | 11/2010 | Sepke | A47L 13/22 55/DIG. 3 |
| 9,399,079 B2 * | 7/2016 | McMinn | C11C 5/002 |
| 10,933,154 B2 * | 3/2021 | Park | A61L 9/12 |
| 12,011,684 B1 * | 6/2024 | Cerro | B01D 46/62 |
| 2005/0169813 A1 * | 8/2005 | D'Amico | A61L 9/042 422/124 |
| 2008/0115670 A1 * | 5/2008 | Hauville | B01D 46/30 96/131 |
| 2010/0254829 A1 * | 10/2010 | Harris | A61L 9/12 417/65 |
| 2011/0209617 A1 * | 9/2011 | Pihlblad | B01D 46/10 55/332 |
| 2011/0268615 A1 * | 11/2011 | Lackey | B01D 46/0038 422/123 |
| 2012/0070320 A1 * | 3/2012 | Ishii | F04D 17/167 417/313 |
| 2013/0175355 A1 * | 7/2013 | Lackey | A61L 9/12 239/57 |
| 2014/0082957 A1 * | 3/2014 | Harris | A61L 9/12 34/239 |
| 2014/0190355 A1 * | 7/2014 | Lackey | A61L 9/12 239/58 |
| 2015/0072611 A1 * | 3/2015 | Harris | A61L 9/122 454/328 |
| 2018/0333672 A1 * | 11/2018 | Moulton | B01D 53/12 |
| 2019/0015539 A1 * | 1/2019 | Sullivan | A61L 9/122 |
| 2019/0134247 A1 * | 5/2019 | Oligie | F04D 29/705 |
| 2021/0308315 A1 * | 10/2021 | Zeng | F04D 29/705 |
| 2022/0258089 A1 * | 8/2022 | Cerro | B01D 39/12 |
| 2024/0256870 A1 * | 8/2024 | Samples | G06F 9/542 |

* cited by examiner

AIR VENTILIZATION SYSTEM FILTER

CROSS REFERENCE TO RELATED APPLICATIONS

This application is a Continuation-in-Part U.S. patent application Ser. No. 18/471,093, filed on Sep. 20, 2023, which itself was a Continuation-in-Part of U.S. patent application Ser. No. 17/174,966, filed on Feb. 12, 2021, now US Patent Publication US2022/0258089 and abandoned, both being incorporated herein by reference.

STATEMENT REGARDING FEDERALLY SPONSORED RESEARCH AND DEVELOPMENT

Not Applicable.

FIELD OF THE INVENTION

This invention relates to filters or filtering processes specially modified for separating gases or vapors, and more particularly to filters using loose particulate filtering material.

BACKGROUND

The iced for effective air filtration system s in residential and commercial environments has been well-documented, particularly for enhancing indoor air quality for health and odor control. Traditional HVAC systems equipped with dust filters have been the standard solution for removing airborne particulates. However, these systems often fail short in addressing undesirable odors and chemical contaminants, leading to the development of various room air filtration units. Despite these advancements, a significant gap remains in effectively addressing air quality issues across different types of air moving systems, including floor registers and portable fans.

Floor registers and portable fans, commonly used in many settings, present unique challenges in air filtration. These systems frequently lack the capability to integrate is advanced filtration solutions effectively, and they are often not equipped to handle additional functionalities such as scent distribution for room freshening. Moreover, the existing solutions for these systems are not always user-friendly, particularly concerning serviceability and maintenance, Filters for these units are often difficult to install, replace, or service, which can discourage regular maintenance and compromise air quality.

There is a clear need for an improved filtration invention that not only efficiently filters out particulates and contaminants but also offers easy maintenance and the ability to enhance the indoor environment with scented materials. Such an invention should be adaptable to various configurations, including floor registers and portable fans, and should allow users to easily service the unit or modify it with scenting materials to freshen the room. This would provide a more holistic approach to indoor air quality management, addressing both cleanliness and ambiance. The present invention accomplishes these objectives.

SUMMARY OF THE INVENTION

The invention described is a filter assembly designed for integration with various air moving systems, including but not limited to HVAC systems and portable fans. The primary structure of the filter assembly consists of two main components: a lower frame and an upper frame, each contributing to the overall functionality of the device.

The lower frame is equipped with a flexible mesh on its bottom side, which together with the frame's perimeter, encloses a lower volume. Within this volume, particulate filter media is loosely contained. This media is crucial for the filtration process, as it moves within the air stream, making an audible noise that not only confirms the system's operation but also aids in the effective filtration of the air.

The upper frame, which can be selectively attached to the lower frame, includes a mesh bottom side and converges at a central hub. This upper frame also defines an upper volume where additional air treatment components can be housed. Notably, the upper frame can contain scenting materials that jostle within the air stream to impart a desired fragrance to the filtered air. This frame is designed to prevent these materials from exiting the frame during operation.

Both frames are designed to be selectively attachable via mechanical fasteners, which can include various types of locking mechanisms. This feature allows for easy maintenance and adjustment of the filter assembly. Additionally, the mesh side of the upper frame is designed to be partially removable to facilitate the easy addition or removal of scenting materials.

Overall, the filter assembly is versatile and adaptable to different air moving systems and configurations, providing not only air filtration but also enhancing air quality with optional scenting features. The design allows for audible feedback and easy maintenance, enhancing user interaction and practicality.

The present invention addresses deficiencies of the prior art by providing an improved filtration system that is not only efficient in filtering out particulates and contaminants but also offers enhanced user-friendliness in terms of maintenance and versatility. This invention is uniquely adaptable to various air moving systems, including floor registers and portable fans, and allows for easy installation and replacement of filter components. Additionally, it incorporates a novel feature that enables the addition of scented materials, effectively transforming the air filtration system into a dual-function unit that also freshens the room environment. This innovative approach not only improves indoor air quality but also enhances the overall user experience by simplifying maintenance and adding customizable scent options, thereby solving the significant challenges faced with existing air filtration technologies. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element. The term "granule size" as used herein refers to largest axis (e.g., diameter of a spherical particle) of the granule. Granule size, or particle size, may also be described with reference to the weight average particle size, as will be understood by those skilled in the art.

Figure 1:
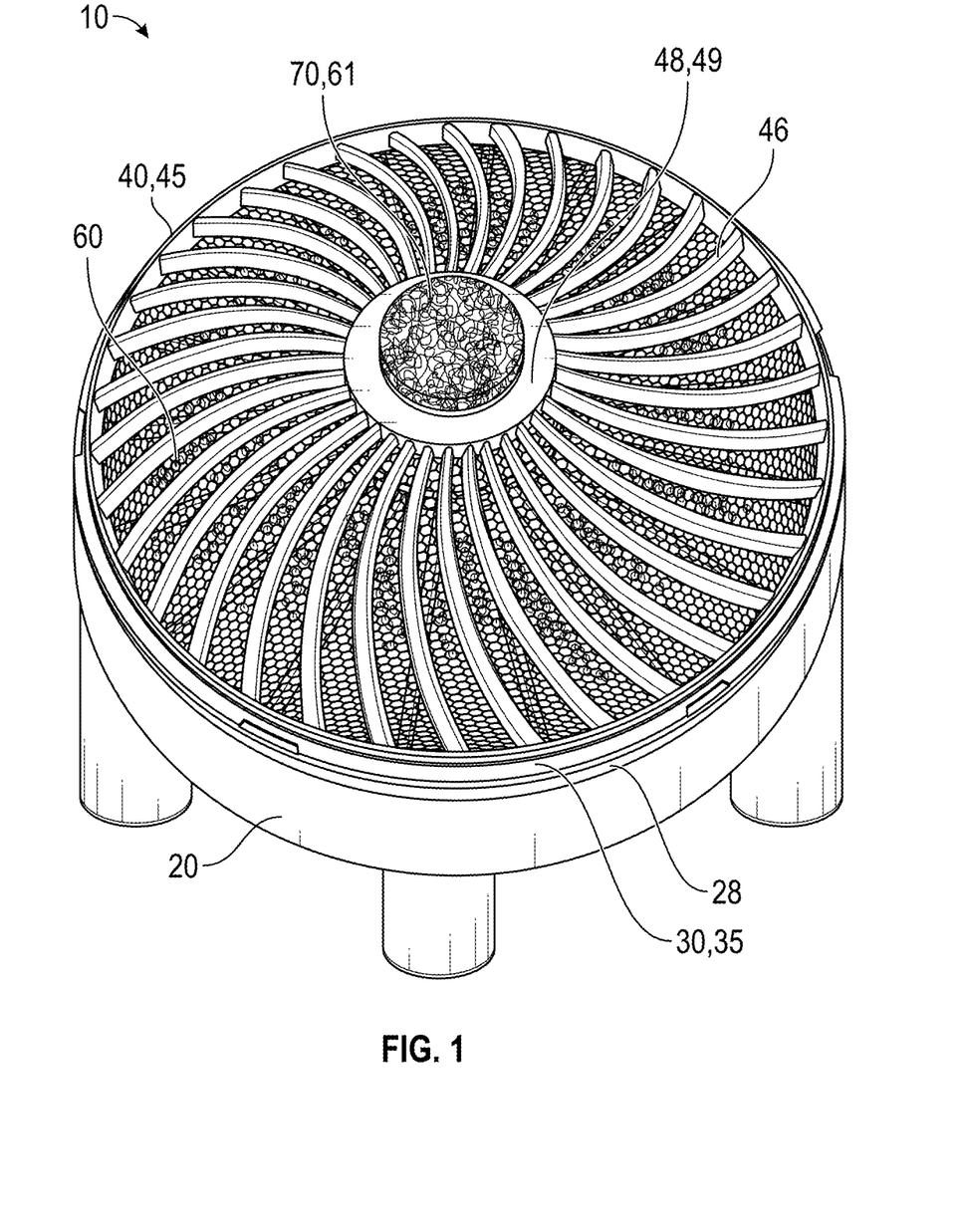
FIG. 1 is a top perspective view of the invention.
Figure 4:
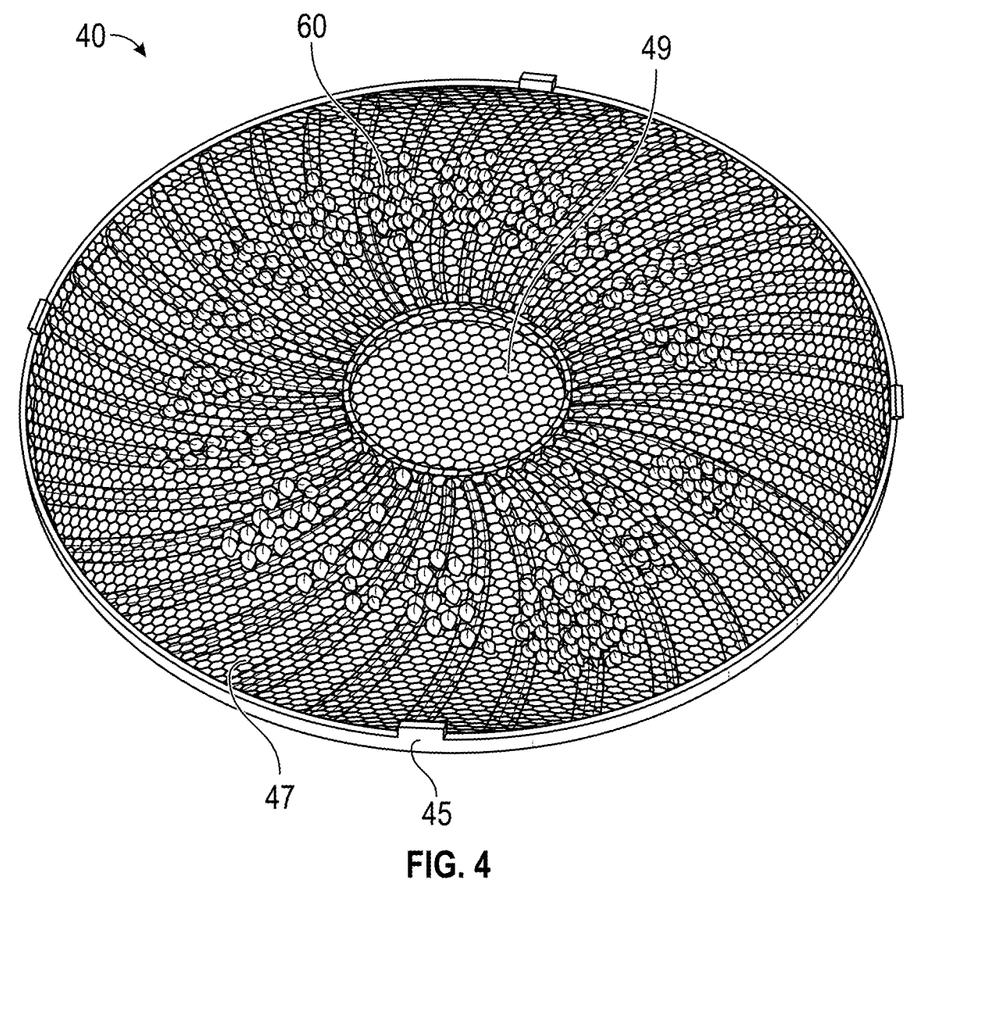
FIG. 4 is a bottom perspective view of the upper frame of the invention.
Figure 5:
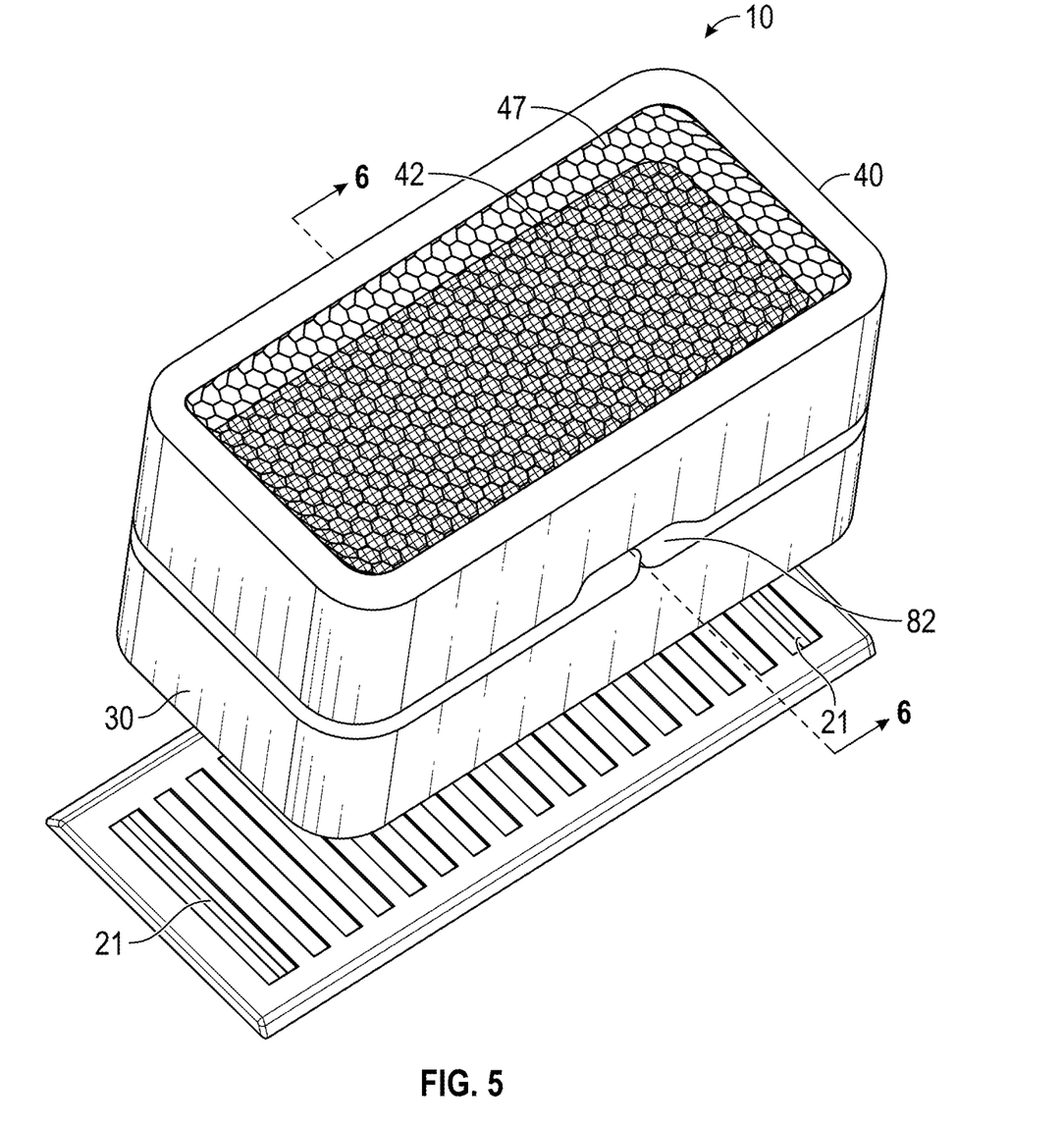
FIG. 5 is a top perspective view of an alternate embodiment of the invention, illustrated in a closed position.

FIGS. 1 and 5 illustrate a filter assembly 10 designed for use with various types of air moving systems 20, including portable fans laid on their sides, HVAC systems with floor registers, within HVAC air ducts, or the like. The filter assembly 10 is particularly adaptable to different configurations as illustrated in the accompanying figures. For instance, in FIGS. 1-4, the air outlet port 28 is depicted as part of a round fan that directs air upwardly, while in FIGS. 5 and 6, the air moving system 20 is a typical HVAC system with floor registers 21, and the filter assembly 10 is shown in a rectangular configuration to suit this setup.

Figure 2:
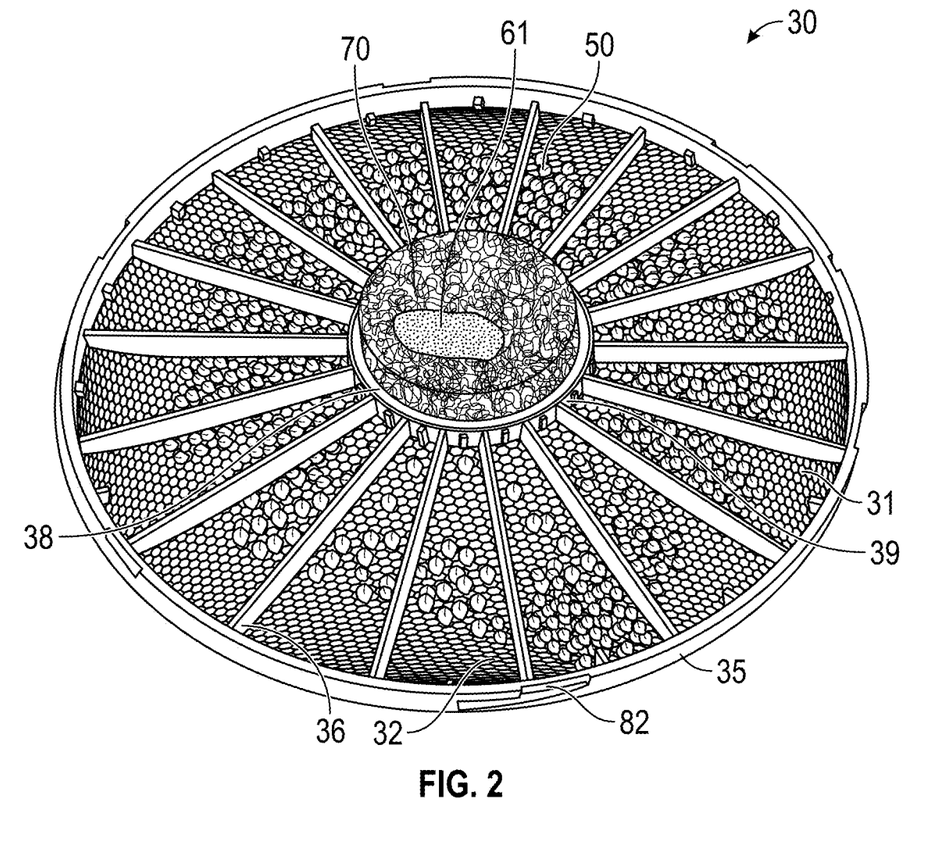
FIG. 2 is a top perspective view of a bottom frame of the invention.

The filter assembly 10 comprises a lower frame 30 with a perimeter 35 fixed with a flexible mesh bottom side 32. The perimeter 35 of the lower frame 30 and the flexible is mesh bottom side 32 define a lower volume 31. Suitable materials for the lower frame 30 include plastics, metals, or composite materials, which provide necessary rigidity and durability. The flexible mesh bottom side 32 may be made with a flexible screen, plastic mesh material, or the like.

Figure 3:
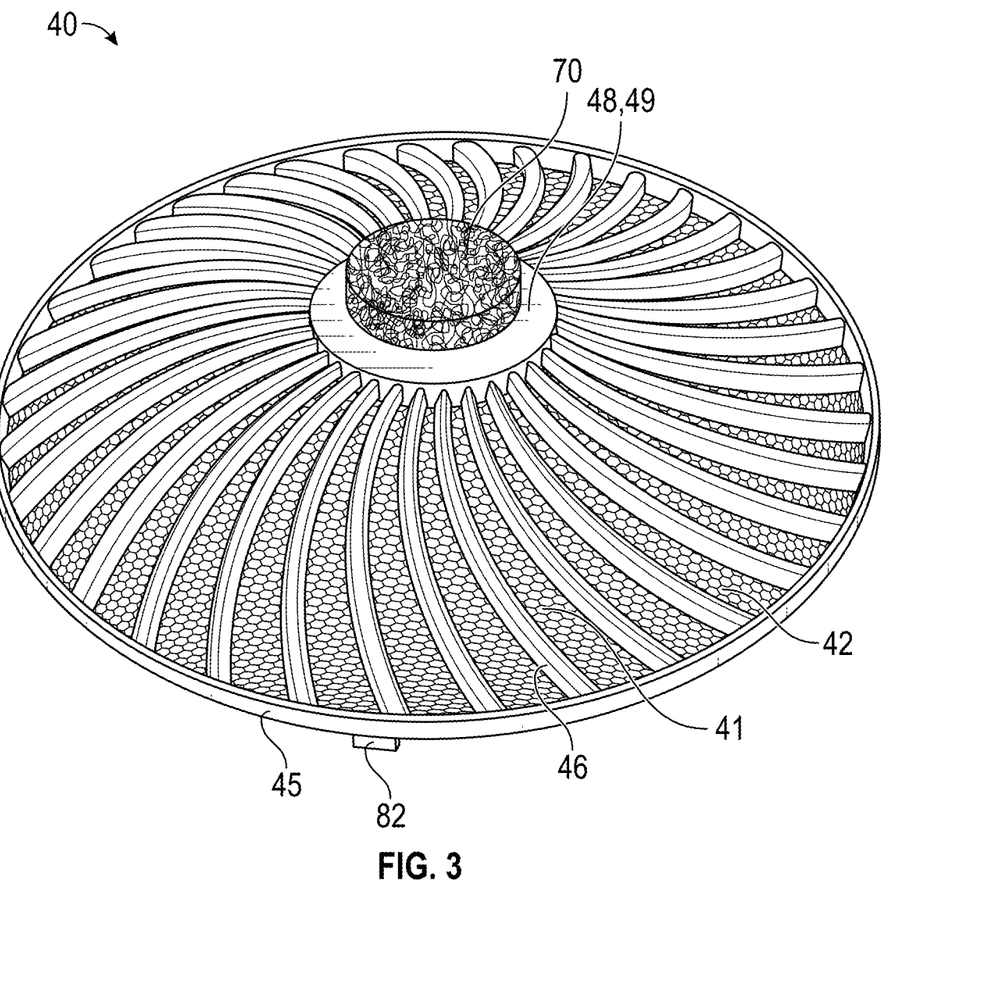
FIG. 3 is a top perspective view of an upper frame of the invention.

An upper frame 40 includes a perimeter 45 that is selectively fixable with the perimeter 35 of the lower frame 30. The upper frame 40 comprises upper frame members 46 converging at a central hub 49 with a top surface 48, and a mesh bottom side 42. The perimeter 45 of the upper frame 40 and the mesh bottom side 42 define an upper volume 41. Materials for the upper frame 40 and its components may include similar materials as the lower frame 30.

Particulate filter media 50 is loosely contained within the lower volume 31, so that it is free to jostle around when the air moving system 20 is activated. When the perimeter 35 of the lower frame 30 is fixed with the perimeter 45 of the upper frame 40, the filter assembly 10 is placed onto the horizontal air outlet port 28 of the air moving system 20. The particulate filter media 50 jostles around in an air stream within the lower volume 31, preferably making an audible clicking noise as granules of the particulate filter media 50 collide in the air stream, thereby effectively filtering the air and providing audible feedback that the air moving system is active. The particulate filter media 50 is preferably made from activated carbon having an average granular size of between 0.6 mm to 1.0 mm. In some embodiments of the invention, the granule activated carbon may have an irregular, non-spherical surface.

In one embodiment, the upper frame 40 also includes an upper mesh side 47 fixed with the upper frame members 46 (FIG. 4). A scenting material 60, when placed within the upper volume 41, jostles around in the air stream within the upper volume 41 to impart a scent to the air stream. The upper mesh side 47 inhibits the scenting material 60 from being blown out of the upper volume 41 of the upper frame 40. The scenting material 60 can be potpourri, rose petals, or other suitable scenting agents. Another embodiment includes the upper frame members 46 together defining a frame mesh 44. The frame mesh 44 inhibits the scenting material 60 from being blown out of the upper volume 41 of the upper frame 40.

Further, the filter assembly 10 may include an absorbent member 70 fixed with the top surface 48 of the upper frame 40. A scenting liquid 61 may be introduced to the absorbent member 70 to impart a scent to the air stream. The absorbent member 70 could be made from materials such as sponges, cloths, or other porous materials suitable for holding liquids. The scenting liquid 61 may be essential oils or other scented liquids, for example.

Figure 6:
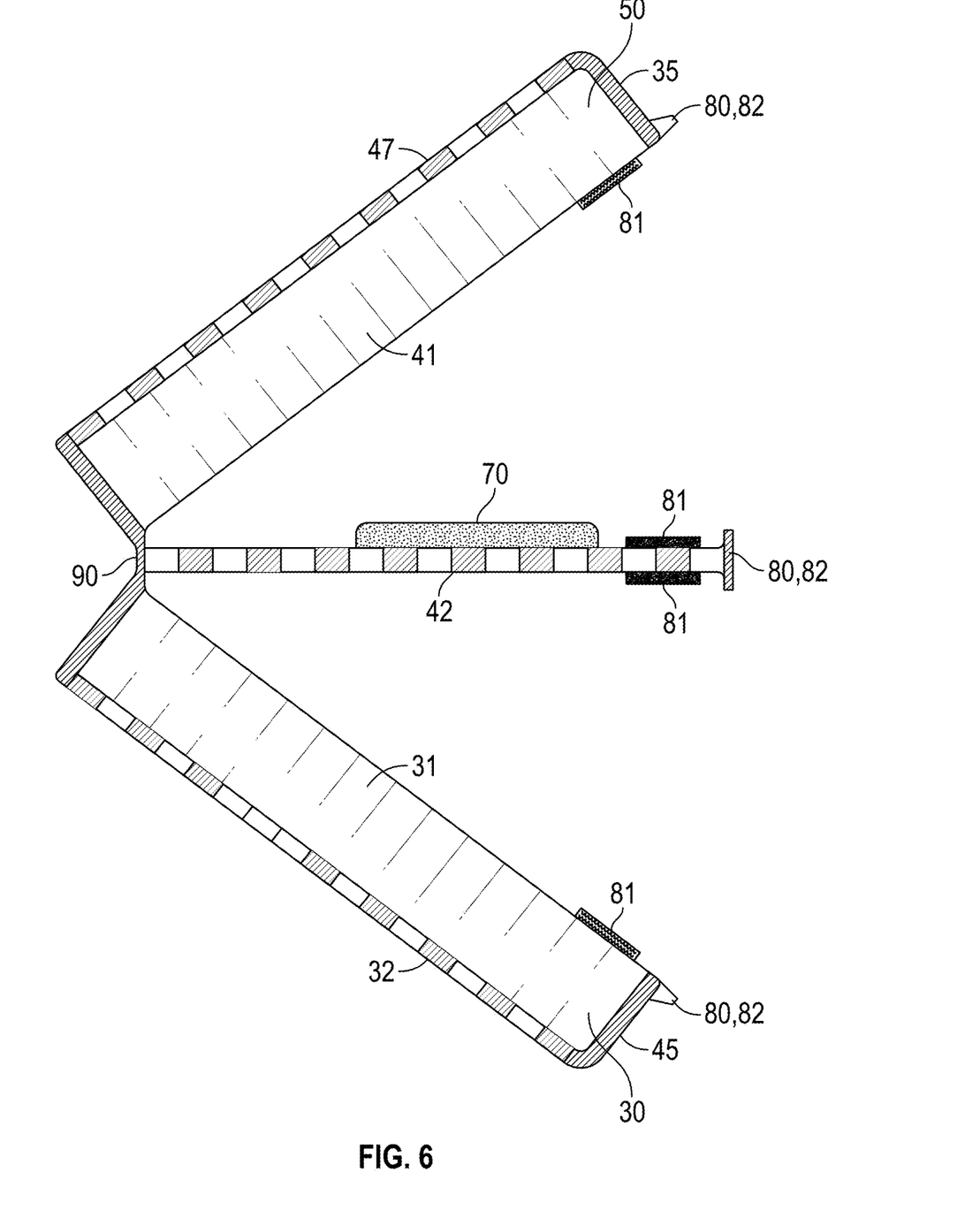
FIG. 6 is a cross-sectional view of the embodiment of FIG. 5, but illustrated in an open position.

The perimeter 45 of the upper frame 40 and the perimeter 35 of the lower frame 30 each have cooperative mechanical fasteners 80, such that the upper frame 40 is selectively fixable with the lower frame 30. Each mechanical fastener 80 includes a hook-and-loop type material 81, a mechanical locking mechanism 82, or the like, providing secure and adjustable attachment. FIG. 6 illustrates both the hook-and-loop type material 81 and mechanical locking mechanism 82, but only one type of mechanical fastener 80 may be used.

Optionally the upper frame 40 and the lower frame 30 are each mutually connected at a living hinge 90 (FIGS. 5 and 6). In such an embodiment, the mesh bottom side 42 can be a more rigid mesh made integrally with the upper frame 40 and the lower frame 30. The mesh bottom side 42 acts to prevent the particulate filter media 50 from mixing with the scenting material 60 when the device is in a closed position (FIG. 5), and separates from both the upper frame 40 and the lower frame 30 when in an open position (FIG. 6) to allow replacement of the particulate filter media 50 and the scenting material 60.

The mesh bottom side 42 of the upper frame 40 is preferably at least partially removable from the perimeter 45 of the upper frame 40 to allow the scenting material to be added to or removed from the upper volume 41. Similarly, disconnecting the upper frame 40 from the lower frame 30 allows the replacement of the particulate filter media 50.

The lower frame 30 may further include lower frame members 36 projecting inwardly to a lower hub 39 that has a top surface 38. An additional absorbent member 70 may be fixed with the top surface 38 of the lower frame 30, whereby a scenting liquid 61 may be introduced to the absorbent member 70 to impart a scent to the air stream.

While a particular form of the invention has been illustrated and described, it will be apparent that various modifications can be made without departing from the spirit and scope of the invention. For example, various shapes of the filter assembly 10 have been illustrated in the drawings. Other shapes may be utilized to accommodate specific air moving systems 20. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention. Changes can be made to the invention in light of the above "Detailed Description."

While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A filter assembly (10) for an air moving system (20) having a horizontal outlet port (28), the filter assembly comprising:
    a lower frame (30) having a perimeter (35) fixed with a flexible mesh bottom side (32), the perimeter of the lower frame and the flexible mesh bottom side defining a lower volume (31);
    an upper frame (40) having a perimeter (45) selectively fixable with the perimeter of the lower frame, upper frame members (46) meeting in a central hub (49) that has a top surface (48), and a mesh bottom side (42), the perimeter of the upper frame and the mesh bottom side defining an upper volume (41);
    particulate filter media (50) loosely contained within the lower volume;
    whereby with the perimeter of the lower frame fixed with the perimeter of the upper frame, the filter assembly is placed onto the horizontal outlet port of the air moving system to filter air moving through the air moving system, the particulate filter media jostling around in an air stream within the lower volume, making an audible clicking noise as the particulate filter media collides in the air stream, the particulate filter media filtering the air stream.

2. The filter assembly of claim 1 wherein the upper frame includes an upper mesh side (47) fixed with the upper frame members, whereby a scenting material (60) when placed within the upper volume jostles around in the air stream within the upper volume to impart a scent to the air stream, the upper mesh side inhibiting the scenting material from being blown out of the upper volume of the upper frame.

3. The filter assembly of claim 1 wherein the upper frame members together define a frame mesh (44), whereby a scenting material when placed within the upper volume jostles around in the air stream within the upper volume to impart a scent to the air stream, the frame mesh inhibiting the scenting material from being blown out of the upper volume of the upper frame.

4. The filter assembly of claim 1 further including an absorbent member (70) fixed with the top surface of the upper frame, whereby a scenting liquid (61) may be introduced to is the absorbent member to impart a scent to the air stream.

5. The filter assembly of claim 1 wherein the perimeter of the upper frame and the perimeter of the lower frame each have cooperative mechanical fasteners (80), such that the upper frame is selectively fixable with the lower frame.

6. The filter assembly of claim 5 wherein each mechanical fastener includes a hook-and-loop type material (81).

7. The filter assembly of claim 5 wherein each mechanical fastener includes a mechanical locking mechanism (82).

8. The filter assembly of claim 1 wherein the mesh bottom side of the upper frame is at least partially removable from the perimeter of the upper frame to allow a scenting material to be added to or removed from the upper volume.

9. The filter assembly of claim 1 wherein the lower frame further includes lower frame members (36) projecting inwardly to a lower hub (39) that has a top surface(38).

10. The filter assembly of claim 9 further including an absorbent member (70) fixed with the top surface of the lower frame, whereby a scenting liquid (61) may be introduced to the absorbent member to impart a scent to the air stream.

11. A filter assembly for an air moving system having a horizontal outlet port, the filter assembly comprising:
    a lower frame having a perimeter fixed with a flexible mesh bottom side, the perimeter of the lower frame and the flexible mesh bottom side defining a lower volume;
    an upper frame having a perimeter selectively fixable with the perimeter of the lower frame, upper frame members meeting in a central hub that has a top surface, and a mesh bottom side, the perimeter of the upper frame and the mesh bottom side defining an upper volume;
    particulate filter media loosely contained within the lower volume, whereby with the perimeter of the lower frame fixed with the perimeter of the upper frame, the filter assembly is placed onto the horizontal outlet port of the air moving system to filter air moving through the air moving system, the particulate filter media jostling around in an air stream within the lower volume, making an audible clicking noise as the particulate filter media collides in the air stream, the particulate filter media filtering the air stream;

an upper mesh side fixed with the upper frame members, whereby a scenting material when placed within the upper volume jostles around in the air stream within the upper volume to impart a scent to the air stream, the upper mesh side inhibiting the scenting material from being blown out of the upper volume of the upper frame;

an absorbent member fixed with the top surface of the upper frame, whereby a scenting liquid may be introduced to the absorbent member to impart a scent to the air stream;

cooperative mechanical fasteners on the perimeter of the upper frame and the perimeter of the lower frame, such that the upper frame is selectively fixable with the lower frame, wherein each mechanical fastener includes a mechanical locking mechanism;

the mesh bottom side of the upper frame being at least partially removable from the perimeter of the upper frame to allow the scenting material to be added to or removed from the upper volume;

lower frame members projecting inwardly to a lower hub that has a top surface;

an additional absorbent member fixed with the top surface of the lower frame, whereby a scenting liquid may be introduced to the absorbent member to impart a scent to the air stream.

* * * * *